United States Patent [19]

Kondo et al.

[11] 4,250,010

[45] Feb. 10, 1981

[54] INTEGRATED ION SELECTION ELECTRODE DEVICE

[75] Inventors: Asaji Kondo; Masao Kitajima; Isamu Hatanaka, all of Asaka, Japan

[73] Assignee: Fuji Photo Film Corporation, Minami-ashigara, Japan

[21] Appl. No.: 87,855

[22] Filed: Oct. 24, 1979

[30] Foreign Application Priority Data

Oct. 27, 1978 [JP]  Japan .................. 53-148087[U]

[51] Int. Cl.³ .......................................... G01N 27/30
[52] U.S. Cl. ......................... 204/195 M; 204/195 R; 204/195 B
[58] Field of Search .......... 204/195 M, 195 R, 195 B; 128/635

[56] References Cited

U.S. PATENT DOCUMENTS 4,020,830  5/1977  Johnson et al. ................. 204/195 M
4,053,381  10/1977  Hamblen et al. ................. 204/195 M
4,133,735  1/1979  Afromowitz et al. ...... 204/195 M X Primary Examiner—G. L. Kaplan
Attorney, Agent, or Firm—Sughrue, Rothwell, Mion, Zinn and Macpeak

[57] ABSTRACT

An ion selection electrode device for measuring concentrations of predetermined ions such as in biological samples in which measuring electrodes are disposed on a planar substrate with their active heads lying within a circle of small radius. A small sample of a liquid to be measured is dropped on and spreads over the circle contacting each electrode. In a preferred embodiment, two sets of electrodes are provided around adjacent circles on a single substrate, one for the sample and the other for a standard reference fluid. A dam separates the two liquids but electrical contact therebetween is provided by a porous bridge.

3 Claims, 3 Drawing Figures

INTEGRATED ION SELECTION ELECTRODE DEVICE

DESCRIPTION OF THE PRIOR ART

The invention relates to an ion selection electrode integrated board in the form of a sheet for potentiometrically measuring the concentrations of particular ions contained in an aqueous solution and particularly in a mixed ion aqueous solution which is typically a body fluid such as blood or urine. Yet more particularly, the invention relates to a sheet-shaped ion selection electrode integrated board in which various dry-type ion selection electrodes are arranged adjacent to one another on an electrically insulating supporting board in such a manner that the heads of the electrodes are arranged around a circle adjacent to one another so that a variety of ions can be measured by a single action of dropping an aqueous solution sample onto only one spot on a surface.

The measurement of the concentrations of inorganic ions such as $K^+$, $Na^+$, $Ca^+$, $Cl^-$ and $HCO_3^-$ in body fluid is important in clinical medicine. For this measurement, a method in which wet-type ion selection electrodes are used, has been employed.

In the conventional method, the measurement is carried out by immersing rod-shaped electrodes in the body fluid. The method has proven to be rather troublesome in terms of maintenance, cleaning, conditioning, service life and damage to the electrodes. Furthermore, it is necessary to sufficiently immerse the electrodes into the liquid sample to be examined in the cup for every measurement, therefore making it necessary to provide at least several hundreds of micro-liters ($\mu l$) for each sample.

In order to eliminate these difficulties, an electrode device of the type wherein the electrodes are in the form of a film or a wire and a liquid sample to be examined is dropped thereon has been disclosed in Japanese Laid-Open patent application No. 142584/1977 and U.S. Pat. No. 4,053,381, and an electrode device which is made in the form of a sheet by connecting pairs of dry-film type electrodes has previously been disclosed in U.S. Pat. No. 4,053,381. In addition, a method by which the electrodes are assembled in the form of a thin wire has been disclosed in U.S. Pat. No. 3,856,649.

The structure of the dry-type ion selection electrode is in the form of a dry-film which is produced by laminating a metal layer, a layer of non-water-soluble salt of the same metal as that of the metal layer, an electrolytic layer containing anions in common with the non-water-soluble salt, and an ion selection membrane layer on an electrically insulating film in that order, or in the form of a dry wire which is produced by coaxially covering a metal wire with a layer of a non-water-soluble salt of the same metal as that of the metal wire, an electrolytic layer containing anions in common with the non-water-soluble salt, and an ion selection membrane layer in such order.

Depending on the type of the uppermost layer, the ion selection membrane, the dry-type ion selection electrode can measure a particular ion. Accordingly, there are available a variety of membranes such as those used for the measuring ions of $K^+$, $Na^+$, $Cl^-$, etc.

For quantitatively measuring ions in a mixed ion aqueous solution using the above-described dry-type ion selection electrodes, the following method is employed. The electrodes are paired, bridged and connected to a potentiometer. Thereafter, a liquid sample to be examined and a standard (reference) liquid are dropped onto the electrodes and the potential difference developed between the electrodes is measured with the potentiometer.

Accordingly, if the method is employed for quantitatively measuring five different ions, it is necessary to drop the liquid sample onto the electrode five times and also to drop the standard liquid onto the electrode five times. That is, the liquid dropping operation must be carried out ten times in total. It is rather troublesome to drop the liquids this many times. In the case of a clinical chemical examination, it is typically necessary to perform the liquid dropping operation five times per patient. Accordingly, if there are many patients to be examined, then the number of dropping operations may be multiplied considerably.

SUMMARY OF THE INVENTION

This difficulty can be eliminated if it is possible to measure a variety of ions merely by performing the liquid dropping operaton only once. The inventor has found that this can be achieved by concentrating the heads of the ion selection electrodes in one location.

An object of the present invention is thus to provide an ion selection electrode integrated board with which a variety of ions can be quantitatively measured merely by performing the liquid dropping operation once.

Provided according to the invention is an ion selection electrode integrated board including, in order, a supporting board having an electrically insulating surface, at least two different types of ion selection electrodes each of which is in the form of a film or a line produced by laminating a metal layer or metal wire, a layer of a non-water-soluble salt of the metal, an electrolytic layer containing anions in common with the non-water-soluble salt, and an ion selection membrane on the supporting board. The ion selection electrodes are planarly arranged on the supporting board in a circle in such a manner that the heads of the ion selection electrodes are as close to one another as possible without being in electrical contact with on another. Each electrode is covered with a non-water-permeable and electrically insulating membrane with only the ion selection membrane exposed.

In this connection, the fact that the heads of the ion selection electrodes are as close to one another as possible means that the heads of the ion selection electrodes are arranged as close to one another as possiblẽ to the extent that when the liquid sample is dropped, it spreads on the supporting board and wets the latter. In the case where the amount of liquid sample for one liquid dropping operation is about 100 $\mu l$, the range of spreading of the dropped liquid sample on the supporting board is a circle with radius of about 2 cm at the maximum. Accordingly, the fact that the heads of the ion selection electrodes are as close to one another as possible means that the heads should be arranged in the circle with radius of about 2 cm or less. However, this is not limitative in the case where the amount of dropped liquid sample is more than 100 $\mu l$ as the liquid sample can spread over a larger range.

The electrodes are planarly arranged fixedly secured to the surface of the supporting board (in contact therewith). An arrangement of the electrodes in parallel with one another or radially extending from one particular point is convenient for manufacturing and operating the ion selection electrode integrated board. However, the electrodes may be disposed in other arrangements.

The fact that each ion selection electrode is covered with the non-water-permeable and electrically insulating membrane with only the ion selection membrane exposed implies that in each of the ion selection electrodes arranged on the surface of the supporting board, only the surface of the ion selection membrane away from the supporting member or only the layers above the electrolytic layer are exposed while the remaining parts of the electrode are covered with a non-water-permeable and preferably electrically insulating membrane. The ion selection electrode integrated board may be so designed that only the electrodes are covered with the electrically insulating membrane or both the electrodes and the surfaces of the supporting member between the electrodes are covered therewith.

It is preferable that electrical contact terminals, whose number is equal to the number of the ion selection electrodes, are provided on the peripheral portion of the supporting board and that electrical wiring circuits are provided between the electrical contact terminals and the ion selection electrodes in such a manner that the electrical wiring circuits are not in contact with one another. The electrical contact terminals and the electrical wiring circuits can be provided by using conventional electrically conductive material in a conventional manner. For instance, the electrically conductive material may be copper, aluminum, or silver or an electrically conductive paint containing particles of such materials. The electrical wiring circuits and the electrical contact terminals may be provided for instance in accordance with a conventional printed wiring circuit forming method using photoresist, a method of applying an electrically conductive paint using a template, or a printing method using an electrically conductive paint. It is obvious that the integrated board can be so designed that the electrical wiring circuits and the electrical contact terminals are eliminated therefrom and the electrodes of a potential difference measuring device are brought in direct contact with the ion selection electrodes fixedly arranged on the supporting board.

A device for quantitatively measuring ions which is provided with an ion selection electrode integrated board according to the principle of the present invention is constructed as follows. The device includes two sets of ion selection electrode integrated units on a supporting board having an electrically insulating surface. Each of the integrated units includes at least two different types of ion selection electrodes each of which is in the form of a film or a line produced by laminating a metal layer or a metal wire, a layer of a non-water-soluble salt of the metal, an electrolytic layer containing anions common with the non-water-soluble salt, and an ion selection membrane that. The ion selection electrodes are planarly arranged on the supporting board in such a manner that the heads of the ion selection electrodes are as close to one another as possible to the extent that the ion selection electrodes are not in electrical contact with one another. Each electrode is covered with a non-water-permeable and electrically insulating membrane with only the ion selection membrane exposed. The inventive ion selection electrode integrated board device further may include a belt-shaped protrusion provided between the integrated units, the protrusion being made of a non-water-permeable and electrically insulating material long and high enough to separate the integrated units, and a belt-shaped bridge provided on the supporting board, the bridge being made of a porous material extending over the protrusion substantially to the centers of the ion selection electrode groups arranged respectively on the integrated units. Still further, the device may include contact terminals provided on the supporting board, the number of which is equal to the number of the ion selection electrodes, and electrical wiring circuits electrically insulated from one another and provided between the contact terminals and the ion selection electrodes.

In the above-described device, the center of the ion selection electrodes arranged adjacent to one another is the center of the range over which a dropped liquid sample spreads over the supporting board. In the case where the electrodes are arranged radially from a center point, this one point is the center from which spreading occurs. In the case where the ion selection electrodes are arranged in parallel with one another, the center is the point on a straight line passing along the middle ion selection electrode, which point is separated from the end of the electrode but is adjacent thereto. The belt-shaped protrusion may be formed by using the same non-water-permeable and electrically insulating material as that covering the ion selection electrode or it may be formed using other materials. The belt-shaped bridge is made of a porous material, preferably a material having continuous fine holes or minute bubbles. Examples of such material are an isotropical porous membrane (a membrane filter), an ionotropic porous membrane, a membrane filter containing minute spherical particles, a porous film or layer produced by dispersing minute spherical particles in a macromolecular material capable of forming a film, and a formed macromolecular material film having minute bubbles. The bridge can be constructed by cutting any of these materials to the desired width and length and bonding the cut material to a supporting board or a non-water-permeable and electrically insulating film with a conventional adhesive. Furthermore, the bridge may be constructed as follows. First, the material in molten form or dissolved in a solvent is coated on the supporting board or the film to provide a bridge having a desired configuration. If necessary, the bridge may be shaped by an after-treatment such as heating.

DESCRIPTION OF THE PREFERRED EMBODIMENTS OF THE INVENTION

The ion selection electrode arrangement and operation in accordance with the invention will first be described with reference to FIGS. 1 and 2.

Figure 1:
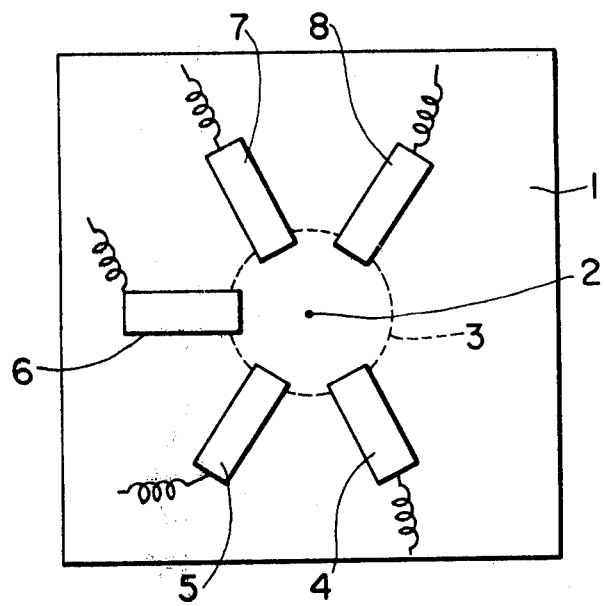
FIG. 1 is a plan view of an ion selection electrode integrated board according to the invention.

In an ion selection electrode integrated board of the invention as shown in FIG. 1, portions of the heads of various electrodes are arranged in a circle 3 with radius of about 2 cm and with center at a point 2 on an electrically insulating supporting board 1. That is, various dry-film-shaped ion selection electrodes 4, 5, 6, 7 and 8 are radially arranged and fixed on the supporting board 1. Accordingly, when one drop of liquid sample to be examined is allowed to fall onto the point 2 on the supporting board 1, it spreads within the circle 3 to wet all of the electrode heads.

In order to prevent the electrodes from being short-circuited by the liquid sample thus dropped, the ion selection membrane of each electrode is exposed, but the remaining portions of each electrode are protectively covered with a non-water-permeable, electrically insulating film so that no water is allowed to permeate therethrough. If the electrodes are set as close to one another as possible to the extent that they are not in contact with one another, then the amount of liquid sample to be dropped can be readily reduced to 100 $\mu$l or less.

Examples of preferred materials for the electrically insulating supporting board are paper, synthetic paper, plastic film (such as polymethylmethacrylate film, polyethyleneterephthalate film, cellulose diacetate film, or cellulose triacetate film), and a compound supporting material produced by coating or laminating plastic on paper.

Figure 2:
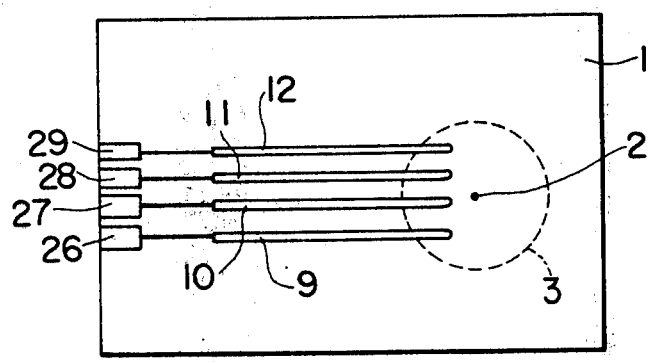
FIG. 2 shows another example of the ion selection electrode integrated board in which wire-shaped ion selection electrodes are arranged in parallel with one another.

In an ion selection electrode integrated board as shown in FIG. 2, all of electrode heads are positioned within a circle 3 having a radius of about 2 cm and with center at a point 2 on an electrically insulating supporting board 1. The various dry-type wire-shaped ion selection electrodes 9, 10, 11 and 12 are arranged in parallel with one another on the supporting board 1. Electrical contact terminals 26, 27, 28 and 29 are provided on the supporting board 1 and are connected through electrical wiring circuits to the respective ion selection electrodes.

Figure 3:
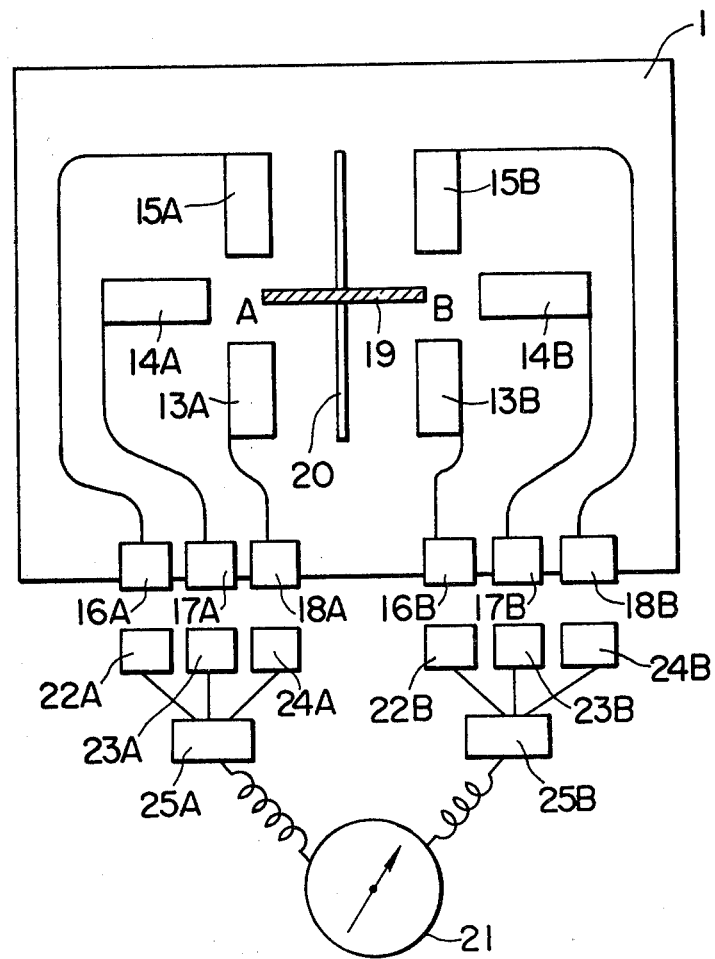
FIG. 3 is an explanatory diagram showing a specific example of a multi-ion selection electrode integrated board according to the invention.

A specific example of an ion selection electrode integrated board for measuring three different ions $K^+$, $Na^+$ and $Cl^-$ and which utilizes the principle of the present invention is shown in FIG. 3. In this example, pairs of various dry-film-type selection electrodes, namely a pair of selection electrodes 13A and 13B for ions $K^+$, a pair of selection electrodes 14A and 14B for ions $Na^+$ and a pair of selection electrodes 15A and 15B for ions $Cl^-$, are radially arranged in such a manner that the electrodes 13A, 14A and 15A surround a point A on three sides while the electrodes 13B, 14B and 15B surround on three sides a point B on an acrylic resin board 1 having a thickness of 1 mm. The heads of the electrodes 13A–15A are arranged in a circle having a diameter of about 1 cm while similarly the heads of the remaining electrodes 13B–15B are arranged in a circle with diameter of about 1 cm. The wiring circuits of the electrodes are connected to contact terminals 16A, 17A, 18A and 16B, 17B and 18B, respectively, as indicated by the solid lines in FIG. 3. A thread-shaped or belt-shaped bridge 19 made of a porous sheet material is provided so as to connect the points A and B in such a manner that the bridge is mounted over a dam 20 which is a ridge-like protrusion made of an electrically insulating and non-water-permeable material.

In order to measure three different ions in a blood sample using this ion selection electrode integrated board, the integrated board is connected to a potentiometer as follows. The integrated board is electrically connected through the contact terminals 16A, 17A, 18A, 16B, 17B and 18B to the contact sockets 22A, 23A, 24A, 22B, 23B and 24B respectively of a potential difference measuring device 21, such as an analog indication-type potentiometer, in a conventional manner. In FIG. 3, reference characters 25A and 25B designate switch devices which operate to switch the contacts so that the selection electrodes for the same ion are selected. That is, the switch devices 25A and 25B successively connect the ion electrodes 13A and 13B, 14A and 14B and 15A and 15B to the potential difference measuring device in pairs. In the integrated board shown in FIG. 3, for instance two-pole triple-throw interlocking switches can be employed for the switch devices. The employment of such interlocking switches is preferable to facilitate the contact change-over operation and to prevent erroneous operation such as simultaneous selection of electrodes for different ions.

Operationally, about 50 $\mu$l of blood serum is dropped onto the point A, after which about 50 $\mu$l of mixed ion standard aqueous solution is dropped onto the point B. In this case, the dam 20 prevents the two liquids from mixing with one another. Each of the two liquids spreads substantially semi-circularly to wet the respective electrodes and the bridge 19 to thereby form an electrical bridge between the two liquids. As a result, potential differences are produced corresponding to the concentrations of the different ions in the blood serum. Accordingly, if the circuits are successively switched to read the indicated values on the potential difference measuring device, then the concentrations of the ions $K^+$, $Na^+$ and $Cl^-$ can quantitatively be determined.

As is believed clear from the above description, an ion selection electrode integrated board according to the invention has the following characteristics and difference with regard to prior art constructions.

(1) A conventional ion selection electrode device is bulky because it has a cubic structure in which the electrodes are inserted into a sample liquid cup. In contrast, the ion selection integrated board according to the invention is planar and thus far more compact.

(2) Since the ion selection electrode integrated board of the invention is entirely of the dry type, its stability with regard to storage time is high.

(3) A variety of ions can be measured merely by dropping about 100 $\mu$l or less of liquid sample one time.

(4) With the ion selection electrode integrated board of the invention, the wasteful cleaning operation required by the prior art constructions is eliminated.

(5) The operation can be achieved with only one action and no liquid waste material is created.

What is claimed is:

1. An ion selection electrode device comprising:
a supporting board having an electrically insulating surface;
a plurality of pairs of electrodes, each of said pairs being arranged on said supporting board, a first electrode of each of said pairs of electrodes having a head thereof positioned within a first circle and a second electrode of each of said pairs of electrodes having a head thereof positioned within a second circle, each of said electrodes comprising, in order, a metal substrate laminated with a layer of a non-water-soluble salt of said metal, an electrolytic layer containing anions in common with said non-water-soluble salt, and an ion selection membrane, each electrode of said pairs of electrodes having a like ion selection membrane and the ion selection membranes being different between at least some of said pairs of electrodes;
a non-water-permeable and electrically insulating membrane covering each of said electrodes with only said ion selection membranes exposed;

an insulating ridge positioned between said two circles; and a bridge of porous material extending over said ridge.

2. The ion selection electrode device of claim 1 wherein the radius of each of said circles is no greater than 2 cm.

3. The ion selection electrode device of either claim 1 or 2 further comprising:

electrical connection means coupled to each of said electrodes; and two switch means, a first one of said switch means being coupled to said first electrodes of said pairs of electrodes and a second one of said switch means being coupled to said second electrodes of said pairs of electrodes, said two switches coupling a selected pair of electrodes to external utilization means, said switches operating in parallel with one another.

* * * * *